US005672760A

United States Patent [19]

Burns et al.

[11] Patent Number: 5,672,760
[45] Date of Patent: Sep. 30, 1997

[54] ABLATIVELY PHOTODECOMPOSABLE COMPOSITIONS

[75] Inventors: Francis Charles Burns, Apalachin, N.Y.; William Weathers Fleming, Virginia Beach, Va.; Victor Yee-Way Lee, San Jose, Calif.; Randy William Snyder, Vestal, N.Y.

[73] Assignee: International Business Machines Corporation, Armonk, N.Y.

[21] Appl. No.: 629,649

[22] Filed: Apr. 9, 1996

Related U.S. Application Data

[62] Division of Ser. No. 476,760, Jun. 7, 1995.

[51] Int. Cl.⁶ .................................................. C07C 317/32
[52] U.S. Cl. .......................... 564/440; 556/410; 564/412; 564/441; 564/433
[58] Field of Search .............................. 564/440, 412, 564/441, 443; 556/410

[56] References Cited

U.S. PATENT DOCUMENTS

| | | | |
|---|---|---|---|
| Re. 28,789 | 4/1976 | Chang | 522/13 |
| 3,867,318 | 2/1975 | Nishikubo et al. | 526/320 |
| 3,985,566 | 10/1976 | Buhr et al. | 526/328.5 |
| 4,720,470 | 1/1988 | Johnson | 437/173 |
| 4,839,261 | 6/1989 | Nakazaki et al. | 430/313 |
| 4,861,425 | 8/1989 | Greer et al. | 430/315 |
| 4,877,853 | 10/1989 | Siol et al. | 526/329.7 |
| 4,902,610 | 2/1990 | Shipley | 430/312 |
| 4,913,836 | 4/1990 | East | 526/328 |
| 4,957,655 | 9/1990 | Khanarian et al. | 526/310 |
| 4,975,223 | 12/1990 | Doi et al. | 526/346 |
| 4,978,476 | 12/1990 | Allen et al. | 526/328 |
| 5,002,361 | 3/1991 | DeMartino et al. | 350/96.12 |
| 5,017,502 | 5/1991 | Sakama et al. | 437/2 |
| 5,041,509 | 8/1991 | Lee et al. | 527/243 |
| 5,043,251 | 8/1991 | Sonnenschein et al. | 430/297 |
| 5,130,227 | 7/1992 | Wade et al. | 430/19 |
| 5,133,898 | 7/1992 | Fock et al. | 252/356 |
| 5,137,618 | 8/1992 | Burnett et al. | 430/270.1 |
| 5,153,103 | 10/1992 | Kotachi et al. | 430/296 |
| 5,178,961 | 1/1993 | Faust et al. | 526/278 |
| 5,178,963 | 1/1993 | Faust et al. | 526/310 |
| 5,186,865 | 2/1993 | Wu et al. | 252/582 |
| 5,196,376 | 3/1993 | Reche | 437/225 |
| 5,207,952 | 5/1993 | Griffin, III | 528/289 |
| 5,231,140 | 7/1993 | Kilburg et al. | 525/275 |
| 5,246,817 | 9/1993 | Shipley et al. | 430/312 |
| 5,262,244 | 11/1993 | Faust et al. | 428/463 |
| 5,384,221 | 1/1995 | Savant et al. | 430/19 |
| 5,401,618 | 3/1995 | Chapman et al. | 205/125 |
| 5,460,921 | 10/1995 | Cywar et al. | 430/314 |

OTHER PUBLICATIONS

Swalen et al., Chemical Abstracts, vol. 118, abstract 243979 1993.

*Primary Examiner*—Richard L. Raymond
*Attorney, Agent, or Firm*—Calfee, Halter & Griswold LLP

[57] ABSTRACT

The present invention provides an ablatively photodecomposable polymer having a photoabsorber bound to the polymer (the "ablatively photodecomposable polymer") which does not phase separate, nor does it crystallize. The ablatively photodecomposable polymer provides even ablation, high resolution and in preferred embodiments, can withstand potassium permanganate etchant and ferric chloride etchant. The ablatively photodecomposable polymer is strippable, although it can remain on the substrate if desired. The ablatively photodecomposable polymer comprises a polymer to which a photoabsorber is bound, either covalently or ionically. The present invention is also directed to a process for forming a metal pattern on a substrate employing the ablatively photodecomposable polymer.

1 Claim, 3 Drawing Sheets

(2 of 3 Drawing(s) in Color)

ABLATIVELY PHOTODECOMPOSABLE COMPOSITIONS

This is a divisional of copending application Ser. No. 08/476,760 filed on Jun. 7, 1995.

BACKGROUND OF THE INVENTION

A method of forming metal patterns on a substrate, particularly forming the patterned circuitry on high density electronic packaging, utilizes a technique termed "ablative photodecomposition." This technique, which is a method of dry imaging, involves depositing an organic polymer coating on the substrate to be patterned. The polymer coating, which is sensitive to radiation, is then patterned by irradiation typically from a laser, usually an excimer laser. A large number of photons of a particular wavelength are directed to the polymer coating in a short time. The polymer coating, which must be capable of absorbing at the laser wavelength, absorbs a significant portion of these photons. As a result, in certain types of laser ablation, many polymer chain fragments are produced in a small volume in a very short time. This causes a localized increase in pressure which cannot be sustained, and the pressure is relieved by the process of ablation, wherein fragmented polymer chains explode and escape from the coating, leaving an etched material. Thus, the material is patterned without a solvent development stage. However, the absorption efficiency of a particular ablatable polymer coating at a particular wavelength may be quite low so that considerable laser energy is required to ablate the polymer coating.

To increase the absorption efficiency of the polymer coating at the particular wavelength to which the polymer coating will be exposed, photoabsorbers have been mixed with the polymers. The photoabsorber is selected which will have an absorbance at or near the wavelength of the laser that will be employed in the ablation.

However, with conventional polymer-photoabsorber mixtures, the photo absorber is not uniformly distributed within the coating. This lack of uniformity arises in part from uneven mixing processes. In addition, over time, lack of uniform photoabsorber distribution develops from crystallization, phase separation, and migration of the photo absorber to the surface or to the interface of the polymer coating and the substrate. As a result of nonuniform distribution of the photoabsorber, increased ablation occurs in the area of the high photoabsorber concentration, leading to poor circuit pattern quality, and poor resolution. Conversely, in areas which have little or no photoabsorber, little or no ablation occurs which often leads to short circuits.

It would be desirable to have an ablatively photodecomposable composition with uniformly dispersed photoabsorber to provide evenly ablated patterns.

SUMMARY OF THE INVENTION

The present invention provides an ablatively photodecomposable polymer having a photoabsorber bound to the polymer (the "ablatively photodecomposable polymer") which does not phase separate, nor does it crystallize. The ablatively photodecomposable polymer provides even ablation, high resolution, and, in preferred embodiments, can withstand potassium permanganate etchant and ferric chloride etchant. The ablatively photodecomposable polymer is strippable, although it can remain on the substrate if desired. The ablatively photodecomposable polymer comprises a polymer to which a photoabsorber is bound, either covalently or ionically.

The present invention is also directed to a process for forming a metal pattern on a substrate employing the ablatively photodecomposable polymer.

The file of this patent contains at least one drawing executed in color. Copies of this patent with color drawings will be provided by the Patent and Trademark Office upon request and payment of the necessary fee.

DETAILED DESCRIPTION OF THE INVENTION

Figure 1:
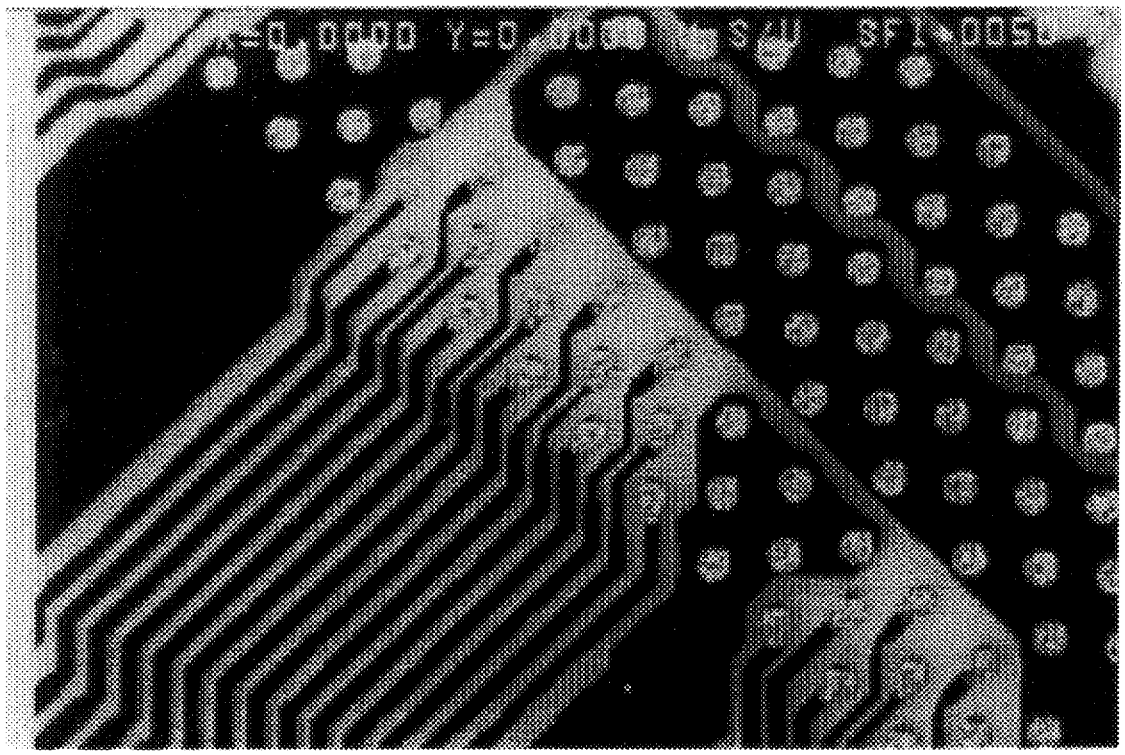
FIG. 1 is a photo of a portion of a circuitization pattern on a ceramic substrate in which the ablatively photodecomposable polymer, DR1-PMMA has been laser ablated; the remaining DR1-PMMA remains over the circuitization lines.

The present invention provides an ablatively photodecomposable polymer having a photoabsorber bound thereto which does not phase separate, or crystallize and which provides even ablation, high resolution and can withstand potassium permanganate etchant, ferric chloride etchant and is strippable. The ablatively photodecomposable polymer comprises a polymer to which a photoabsorber is bound, either covalently or ionically.

The present invention is also directed to a process for forming a metal pattern on a substrate employing the ablatively photodecomposable polymer.

The ablatively photodecomposable polymer preferably comprises polymerized units of an acrylate monomer, more preferably polymerized units of methylmethacrylate, and a photoabsorber which is bound to the polymer. In one embodiment, the photoabsorber is covalently bound to the polymer; preferably where the ablatively photodecomposable polymer is comprised of polymerized units of methylmethacrylate, the photoabsorber is substituted for the methyl group on some or all of the polymerized units of methylmethacrylate. In another embodiment, the photoabsorber is ionically bound to the polymer.

The resolution attainable with the ablatively photodecomposable polymer is 2 microns or less.

The Substrate

The substrate for the ablatively photodecomposable polymer, is preferably an electronic structure, and includes metallized ceramics, multilayer ceramics, metallized ceramic with polyamide, and other conventional substrates.

The Photoabsorber

The photoabsorbers used in the ablatively photodecomposable polymer of the present invention absorb ultraviolet radiation, and will cause or enhance, through the transfer of energy, the ablation of the ablatively photodecomposable composition upon exposure to UV radiation. In the embodiment in which the photoabsorber is covalently bound to the polymer, the preferred photoabsorber is 4[(2 -hydroxyethyl)ethylamino]-4'-(nitrophenyl)azo benzene, commercially available as "Disperse Red Dye-1" from Aldrich Chemical Company, Inc., Milwaukee, Wis. Other suitable photoabsorbers include pyrene, available from Aldrich Chemical Company, Inc., coumarin, available from Aldrich Chemical Company, Inc., 4-[(2-hydroxyethyl)ethylamino]-4'-(trifluoromethylsulfonyl)tolane, and 7-hydroxy-4-methyl-2H-1-benzopyrene-z-one, available from Pfaltz and Baurer Inc. and derivatives thereof. The present invention includes a method for making 4-[(2-hydroxyethyl)ethylamino]-4'-(trifluoromethylsulfonyl)tolane comprising the following steps: first providing (2-hydroxyethyl)ethylaniline; iodinating the (2-hydroxyethyl)ethylaniline to produce 4-[(2-hydroxyethyl) ethylamino]iodobenzene; adding a trimethylsilyl group to the 4-[(2-hydroxyethyl)ethylamino] iodobenzene to produce 4-[(2-trimethylsiloxyethyl) ethylamino]iodobenzene; substituting a trimethylsilylethynyl group for the iodo group on 4-[(2-trimethylsiloxyethyl)- ethylamino]iodobenzene to produce 4-[(2-trimethylsiloxy-ethyl)ethylamino] trimethylsilylethynylbenzene; removing the trimethylsilyl groups on the 4-[(2-trimethylsiloxyethyl)ethylamino]trimethylsilylethynylbenzene to produce 4-[(2-hydroxyethyl) ethylamino]ethynylbenzene; adding 4-trifluoromethylsulfonyl benzene to 4-[(2-hydroxyethyl) ethylamino]ethynylbenzene to produce 4-[(2-hydroxyethyl) ethylamino]-4'-(trifluoromethylsulfonyl)tolane.

The photoabsorbers suitable for use in the ionically bound embodiment include those photoabsorbers that have a tertiary amine functional group that forms a quaternary ammonium salt with an acidic hydrogen on the polymer, and include, for example, 7-(diethylamine)-4-methyl coumarin, available from Aldrich Chemical Company, and 1-(dimethylamino)-pyrene, available from Aldrich Chemical Company, and derivatives thereof.

From abut 1 to 100%, preferably about 5 to 25%, of the polymerized monomers have a photoabsorber bound thereto.

The Ablatively Photodecomposable Polymer

The ablatively photodecomposable polymer has suitable coating properties, and has a weight average molecular weight of at least 15,000, preferably between about 18,000 to about 250,000, most preferably about 25,000.

The ablatively photodecomposable polymer preferably possesses the following properties: chemical resistance; toughness at the temperature of use, which is typically room temperature; good film forming characteristics, that is, the polymer composition dries to a non-tacky, continuous film; and thermal stability, preferably to at least 70° C., more preferably to at least 240° C.

While it is preferred that the ablatively photodecomposable polymer is an acrylate polymer, it should be understood that the photoabsorber may be bound to other polymers including, for example, polyimides.

The Covalently Bound Photoabsorber Embodiment

The ablatively photodecomposable polymer having the photoabsorber covalently bound thereto is preferably an acrylate polymer comprised of polymerized units of an acrylate monomer. Suitable acrylate monomers include, for example, methylmethacrylate, ethylmethacrylate, butylmethacrylate, and mixtures or copolymers thereof. Methylmethacrylate is preferred and is commercially available from E. I dupont de Nemours.

A photoabsorber is covalently bound to the polymer, preferably to all or a portion of the polymerized monomers, so that the photoabsorber is incorporated into the polymer. The ablatively photodecomposable polymer may be formed by first forming a polymer and then attaching the photoabsorber to the polymer, or by first attaching the photoabsorber to an monomer, then polymerizing the photoabsorber-monomer with other monomers.

The Ionically Bound Photoabsorber Embodiment

The ablatively photodecomposable polymer having the photoabsorber ionically bound thereto, is a salt, in which there is an ionic bond between an acid group, preferably an acid hydrogen, on the polymer and a tertiary amine group on a photoabsorber. Thus, the ablatively photodecomposable polymer having the photoabsorber ionically bound thereto is a quartenary ammonium salt. The polymer is preferably an acrylic resin, including, for example, polyacrylic acid, or copolymer of methylmethacrylate and acrylic acid.

Using the Ablatively Photodecomposable Polymer

To apply the ablatively photodecomposable polymer, the ablatively photodecomposable copolymer is dissolved in a solvent to provide a solution containing preferably about 75–95% by weight, solvent. Preferably, the organic solvent permits uniform and easy application of the ablatively photodecomposable polymer coating. Suitable organic solvents include, for example diethylene glycol dimethyl ether, ethyl lactate toluene, acetone, methyl ethyl ketone, methylene chloride, ethyl acetate, tetrahydrofuran, acetonitrile, cyclohexanone, 2-MEE and dimethyl formamide.

The ablatively photodecomposable polymer coating is blanket coated, such as by conventional measures such as roll coating, spraying, blade application or spin coating on top of the electronic structure. Preferably, the ablatively photodecomposable polymer film is about 0.15 to 5.0 micrometers, more preferably about 2 micrometers, in thickness.

Next, the electronic structure is preferably heated to typically between about 70° C. and 150° C. for about 15 to about 30 minutes, to remove the bulk of solvent from the ablatively photodecomposable polymer coating. Then the electronic structure is baked at a final temperature of preferably about 120° C. to about 250° C., for a time sufficient to cure the ablatively photodecomposable polymer. The result is a smooth, hard and uniform ablatively photodecomposable polymer film. The laser or UV lamp is aligned to the electronic structure by conventional means such as an x-y table, or through a photomask. Commercially available excimer lasers typically emit at either 193 nm, 248 nm, 308 nm or 351 nm. Preferably the excimer laser emits a wavelength of about 308 nm.

The ablatively photodecomposable polymer film is then ablated into the desired pattern, using either an excimer laser or a UV lamp. Where the excimer laser is used, a fluence as low as 0.1 J/cm$^2$, will ablate the film; 0.2 J/cm$^2$ is preferred. The number of pulses needed to etch the ablatively photodecomposable polymer film depends on the thickness of the film. The increased photoabsorption efficiency of the ablatively photodecomposable polymer permits efficient ablation at, for example, 0.2 J/cm$^2$, which is not obtainable with conventional mixtures of photoabsorbers and polymer coatings. Also since ablation efficiency is increased, the time required to ablate the ablatively photodecomposable polymer is significantly less.

After the pattern, or mask, is formed in the ablatively photodecomposable polymer, the metal pattern, that is, the circuitization, is created by conventional means. Where the substrate is a metallized ceramic, the metallization is etched. Where the substrate is not metallized, then the pattern created by ablation is metallized by conventional means such as, for example, electroless plating.

The ablatively photodecomposable polymer film can remain on the substrate, or if desired, it is removed with a stripping solvent. Suitable solvents are chosen so that they will selectively remove the ablatively photodecomposable polymer without swelling any surrounding organic dielectric materials. Suitable stripping solvents include, for example, propylene carbonate g-butyrolactone, N-methyl pyrrolidone, ethyl lactate, propylene glycol methyl ether acetate, dimethyl formamide, diethylene glycol dimethyl ether, chloroform, methyl ethyl ketone and methylene chloride.

The following examples illustrate various embodiments of the ablatively photodecomposable polymer.

EXAMPLE 1

The ablatively photodecomposable polymer having the following structure:

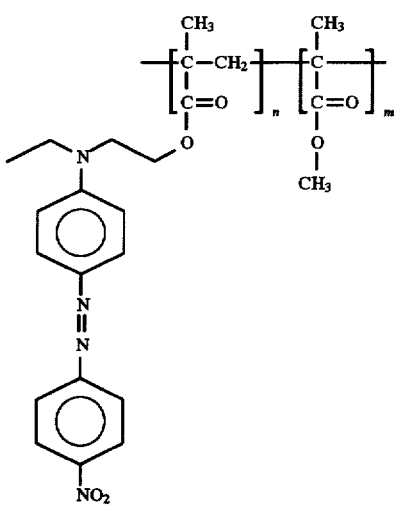

was prepared as follows.

Preparation of 4[(2-Hydroxyethyl)ethylamino]-4'-(nitrophenyl)azo benzene,-Methacrylate Monomer A 1-liter flask equipped with mechanical stirrer, thermometer and dropping funnel was charged with 10 grams, that is, 32 mmoles of purified, 4[(2-hydroxyethyl)ethylamino]-4'-(nitrophenyl)azo benzene, that is, Disperse Red 1 from Aldrich Chemical Company Inc. and 400 ml of methylene chloride. Methacryloyl chloride from Aldrich Chemical Co, was distilled, then 3.2 ml, that is 32.7 mmoles, methacryloyl chloride was added slowly. Next, a solution of 4.7 ml triethylamine in 15 ml of methylene chloride was added at room temperature for 4 hours. If necessary, 0.39 g of dimethylaminopyridine was added to drive the reaction towards completion. The triethylamine and methyl methacrylate, both from Aldrich Chemical Co, were each distilled prior to use.

The reaction mixture was washed with cold 2% aqueous sodium hydroxide followed by deionized water. The organic phase was dried over sodium sulfate. After solvent removal the product was recrystallized from methanol as brown solids to provide 8.8 g, that is a 72% yield. The DR1-methacrylate has a melting point of 92°–93° C., and the following NMR profiling: NMR δ(CDCl$_3$) 8.33 (d, J=9.1 Hz, 2H), 7.98 (d, J=9.1 Hz, 2H), 7.90 (d, J=9.2 Hz, 2H), 6.83 (d, J=9.2 Hz, 2H), 6.12 (t, J=1.0 Hz, 1H), 5.60 (t, J=1.5 Hz, 1H), 4.38 (t, J=6.3 Hz, 2H), 3.75 (t, J=6.2 Hz, 2H), 3.56 (q, J=7.1 Hz, 2H), 1.95 (s, 3H), 1.27 (t, J=7.1 Hz, 3H).

Polymerization of DR1-Methacrylate and Methyl Methacrylate

A reaction tube was charged with: 0.785 g, that is 2.05 mmole, of the 4[(2-hydroxyethyl)ethylamino]-4'-(nitrophenyl)azo benzene,-methacrylate; 2.25 g, that is 22.5 mmol, of methyl methacrylate; 41 mg (0.25 mmole) azo-bis-isobutyronitrile; and 11 ml chlorobenzene. The mixture was stirred and deoxygenated by alternate freeze thaw cycle under vacuum. The tube was sealed under vacuum and heated to 60° C. for 48 hours. The crude product was precipitated with methanol and was repeatedly purified by dissolving in methylene chloride and re-precipitating from methanol.

The red polymer obtained (2.7 g., 90% yield) showed 8% chromophore concentration relative to methylmethacrylate and has average molecular weight of 87,000, number average of 31,000, dispersity of 2.8 measured by GPC. The $T_g$ was 116° C. as measured by DSC.

EXAMPLE 1A

An ablatively photodecomposable polymer was prepared according to Example 1, except that 1.07 g, 2.8 mmole, 4[(2-hydroxyethyl)ethylamino]-4'-(nitrophenyl)azo benzene, methacrylate was added rather than 2.05 mmoles, to provide a ablatively photodecomposable composition having 10% photoabsorber concentration relative to methacrylate.

EXAMPLE 1B

An ablatively photodecomposable polymer was prepared according to Example 1, except that 2.14 g, 5.6 mmole, 4[(2-hydroxyethyl)ethylamino]-4'-(nitrophenyl)azo benzene, methacrylate was added rather than 2.05 mmoles, to provide a ablatively photodecomposable composition having 16% photoabsorber concentration relative to methacrylate.

EXAMPLE 2

The ablatively photodecomposable polymer having the following structure:

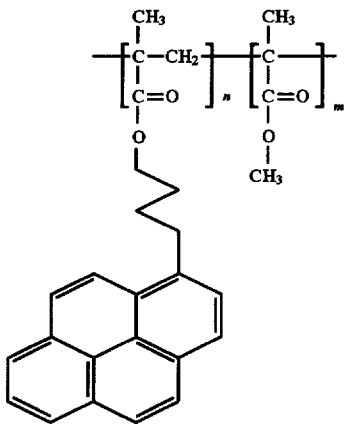

was prepared as explained below.

Preparation of 4-(1-Pyrene)-1-butanol

A 1-liter 3-necked flask equipped with an additional funnel and a reflux condenser was charged with a solution of 2.0 g, that is 52.7 mmol, of lithium aluminum hydride (95%) from Aldrich Chemical Co., in 300 ml dry tetrahydrofuran, also from Aldrich Chemical Co. 1-Pyrenebutyric acid from Aldrich Chemical Co. was recrystallized from toluene, and under a nitrogen atmosphere, a solution of 8.52 g, that is, 29.5 mmol 1-Pyrenebutyric acid in 150 ml THF was added dropwise with magnetic stirring over a period of 1.5 hours. After the addition, the reaction mixture was heated to reflux for 4 hours and then allowed to stir overnight at room temperature. At the end of this time, 2 ml water were added in a dropwise fashion followed by 10 ml 5% NaOH, and the mixture was heated to 35° C. and stirred for 30 minutes. The mixture was then filtered to remove the inorganic solids and the filtrate concentrated on a rotary evaporator to about 150 ml volume. This solution was dried over anhydrous magnesium sulfate for 1 hour and then further concentrated to give an oily residue as a crude product. The oily residue was purified by dissolving the oil residue in about 10 ml methylene chloride and loading onto a 6 in×0.75 in silica gel column, using 86% ethyl ether/14% hexane for elution. Fractions that showed a single spot by thin layer chromatography were combined and the solvent evaporated to give an oil which crystallized upon standing. The final yield of light yellow crystals was 7.55 g (93%). The compound was identified by NMR analysis; NMR (CDCl3) 1.3 ppm (broad, —OH), 1.5–2.2 ppm (m, —CH2—CH2—), 3.37 ppm (m, —CH2—pyrenyl), 3.70 ppm (m, —CH2—O—), 7.8–8.4 ppm (m, pyrenyl-H).

Preparation of 4-(1-Pyrenyl) butyl Methacrylate (Py-MA) Monomer

All operations were performed under yellow safe lights. A 500-ml flask was charged with a solution of 7.55 g, that is 27.6 mmol 4-(1-pyrene)-1-butanol and 5.46 g dry triethylamine (54.0 mmol) in 200 ml anhydrous chloroform, from Aldrich Chemical Co. After purging with nitrogen, the solution was cooled to −5° C. by means of an ice-salt bath and a solution of 4.31 g 41.2 mmol freshly distilled methacryloyl chloride in 75 ml anhydrous chloroform was added dropwise with magnetic stirring over a period of 3 hours. After the addition, the reaction was allowed to warm gradually to room temperature and stirring was continued overnight. Thereafter, 10 ml water was added and the solution stirred for 30 minutes, followed by separation of the organic phase, which was washed sequentially with 20 ml portions of 8% Hcl twice, 5% NaOH twice, and saturated NaCl twice. After drying briefly over MgSO$_4$, a few crystals of 4-methoxy-1-phenol were added to inhibit polymerization and the solvent removed on a rotary evaporator to give an oil which crystallized upon standing. After recrystallization from toluene and drying overnight on a vacuum line at 0.5 mm Hg, a final yield of 5.51 g (58%) was obtained of purified product as a light yellow solid. The compound was identified as 4-(1-pyrenyl) butyl methacrylate, by NMR analysis and comparison of the spectrum with that in the literature (1); NMR (CDCl3) 1.8–2.2 ppm (m, —CH2—CH2—), 3.38 ppm (m, —CH2-pyrenyl), 4.23 ppm (m, —CH2—OOC—), 5.53 ppm (m, =CH2), 6.09 ppm (m, =CH2), 7.8–8.3 ppm (m, pyrenyl-H).

Preparation of 4-(1-pyrenyl) butylmethacrylate-methyl methacrylate polymer

All operations were performed under yellow safe lights. A copolymer of Py-MA and methyl methacrylate (MMA) was prepared as follows. In a 100 ml flask were placed 50 g of propylene glycol monomethyl ether acetate, from Aldrich Chemical Co., 133 mg 2,2'-azobis that is, isobutyronitrile, from Polysciences and a magnetic stir bar. Then 0.0180 g Py-MA and 14.98 g MMA were added for a total of 15.0 g of monomers, the flask capped with a septum, and the mixture stirred at room temperature until dissolution. The solution was purged with nitrogen for 20 minutes and the flask then placed in an oil bath and heated to 65° C. for 24 hours. At the end of this time the oil bath temperature was increased to 100° C. and heating continued for another 24 hours. Stirring and a positive nitrogen pressure were maintained for the entire 48 hour period. To precipitate the polymer, the solution was cooled to room temperature and then added dropwise to 1 liter of rapidly stirred methanol. After filtration and drying, the copolymer was dissolved in either 50 ml chloroform at room temperature and then reprecipitated into 1 liter methanol. After filtration and drying to constant weight under 0.5 mm Hg vacuum, 12.83 g copolymer was obtained.

EXAMPLE 2A

An ablatively photodecomposable polymer was prepared according to Example 2, except that 0.585 g Py-MA was used instead of 0.0180 g, and 14.94 g methyl methacrylate was used instead of 14.98 g, to yield 12.44 g methylmethacrylate - 4-(1-pyrene)butylmethacrylate polymer.

EXAMPLE 2B

An ablatively photodecomposable polymer was prepared according to Example 2, except that 0.1740 g Py-MA was used instead of 0.0180 g, and 14.83 g methyl methacrylate was used instead of 14.98 g, to yield 13.74 g methylmethacrylate - 4-(1-pyrene)butylmethacrylate copolymer.

EXAMPLE 2C

An ablatively photodecomposable polymer was prepared according to Example 2, except that 0.5670 g Py-MA was used instead of 0.0180 g, and 14.43 g methyl methacrylate was used instead of 14.98 g, and after filtration and drying, the copolymer was dissolved in a solution of 50% chloroform/50% toluene at 50° C., to yield 12.42 g methylmethacrylate - 4-(1-pyrene)butylmethacrylate copolymer.

EXAMPLE 2D

An ablatively photodecomposable polymer was prepared according to Example 2C, except that 1.58 g Py-MA was used instead of 0.0180 g, and 13.42 g methyl methacrylate was used instead of 14.98 g, to yield 13.42 g methylmethacrylate - 4-(1-pyrene)butylmethacrylate copolymer.

EXAMPLE 2E

An ablatively photodecomposable polymer was prepared according to Example 2C, except that 4.230 g Py-MA was used instead of 0.0180 g, and 10.77 g methyl methacrylate was used instead of 14.98 g, to yield 13.86 g methylmethacrylate - 4-(1-pyrene)butylmethacrylate copolymer.

EXAMPLE 3

An ablatively photodecomposable polymer in which the photoabsorber is ionically bound to the polymer is prepared by dissolving a copolymer of polymethylmethacrylate and acrylic acid, from Aldrich Chemical Company, in an organic solvent such as, for example, N-methyl-pyrilidone, or propylene glycol monomethyl ether acetate. Next, the photoabsorber, 7 -(diethylamine)-4-methyl coumarin, from Aldrich Chemical Company is added and thoroughly mixed. As the ablatively photodecomposable salt precipitates from solution, it is recovered. The precipitation is completed by adding a counter solvent such as hexane, cyclohexane, tetrahydrofuran or methanol.

EXAMPLE 4

An ablatively photodecomposable polymer in which the photoabsorber is ionically bound to the polymer is prepared by dissolving polyacrylic acid, from Aldrich Chemical Company, in an organic solvent such as, for example, N-methyl-pyrilidone, or propylene glycol, monomtheyl ether and acetate. Next, the photoabsorber, 1-(dimethylamino)-pyrene from Aldrich Chemical Company is added and thoroughly mixed. As the ablatively photodecomposable salt precipitates from solution, it is recovered. The precipitation is completed by adding a counter solvent such as hexane, cyclohexane, tetrahydrofuran or methanol.

EXAMPLE 5

The ablatively photodecomposable polymer having the following structure:

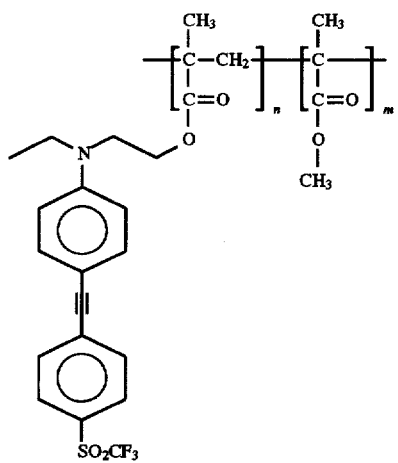

was prepared by first preparing the photoabsorber 4-[12-hydroxyethyl)ethylamino]-4'(trifluoromethyl-sulfonyl)tolane. The synthetic scheme for the 4-[12-hydroxyethyl)ethylamino]-4'-(trifluoromethylsulfonyl)tolane is as follows:

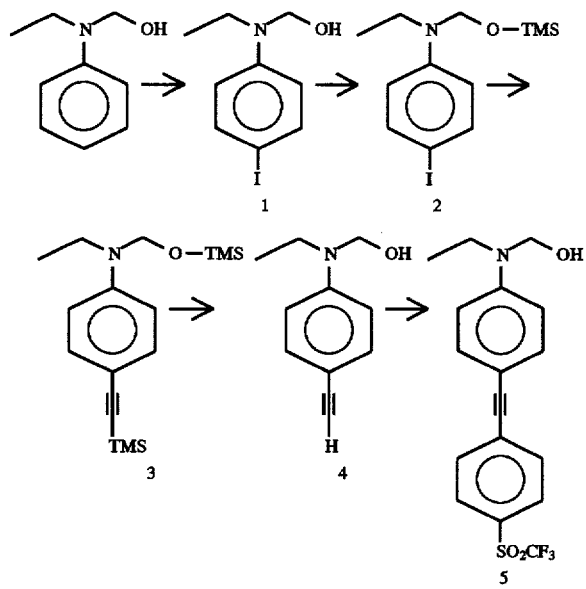

Preparation of Compound 1: 4-[(2-hydroxyethyl)ethylamino]-iodobenzene.

First, 25 g, that is, 150 mmole (2-hydroxyethyl)ethylaniline from Mobay Chemical Corp. was stirred in 20 ml ethanol under nitrogen in a 500 m three-neck flask equipped with a mechanical stirrer. A degassed solution of 25 g, that is 300 mmole sodium bicarbonate in 300 m water was added with stirring. Next, 38.5 g, 150 mmole iodine, from Aldrich Chemical Co., ground in a mortar and pestle was added in portions over a 45 minutes period maintaining the reaction temperature at 20° C. The mixture was stirred for 4 hours, then extracted with chloroform. The organic layer was washed with sodium thiosulfate, from Aldrich Chemical Co. and separated. After removal of the solvent under reduced pressure, decolorizing charcoal was added to the dark residue and extracted repeatedly with hot petroleum ether. A light oil separated and a colorless solid, 4-[(2-hydroxyethyl)ethylamino]iodobenzene, crystallized upon cooling to yield 30 g, at a 68% yield. 4-[(2-hydroxyethyl)ethylamino]iodobenzene has a melting point of 53°–54° C.

Preparation of Compound 2: 4-[(2-Trimethylsiloxyethyl)ethylamino]iodobenzene.

A solution of 14.5 g, that is 50 mmole of 4-[(2-hydroxyethyl)ethylamino]iodobenzene and 6.0 g, that is 60 mmole triethylamine, from Aldrich Chemical Co. in 90 ml tetrahydrofuran ("THF") was stirred in an ice-water bath under nitrogen. Next, 5.5 g, 51 mmole chlorotrimethylsilane, from Aldrich Chemical Co. was added slowly while maintaining the reaction temperature below 10° C. The mixture was stirred for 30 minutes then warmed to room temperature for 1 hour. Ethyl ether was added and extracted with brine. The organic layer was separated and dried over anhydrous sodium sulfate. After removing the solvent under reduced pressure, the residue was flash column chromatographed on silica gel with 2% ethyl acetate-hexane to give 16.63 g of a clear viscous oil at a 92% yield.

Preparation of Compound 3: 4-[(2-Trimethylsiloxyethyl)ethylamino]tri-methylsilylethynylbenzene.

A mixture containing 10.9 g, that is 30 mmole, 4-[(2-trimethylsiloxyethyl)ethylamino]iodobenzene from the previous step, 1.0 g, that is 1.4 mmole bis(triphenylphosphine)palladium(II) chloride from Aldrich Chemical Co., and 74 mg, that is 0.75 mmole cuprous chloride, from Aldrich Chemical Co. in 50 m triethylamine was stirred and degassed under nitrogen for 15 minutes. Next 3.5 g, that is, 36 mmole trimethylsilylacetylene from Aldrich chemical Co. was added with vigorous mechanical stirring at room temperature and the final mixture was stirred at 80° C. for 1 hour. The cooled reaction mixture was filtered, diluted with ethyl ether and extracted with dilute HCL. The organic phase was separated, dried over anhydrous sodium sulfate, and the solvent was removed under reduced pressure. The dark residue was flash column chromatographed on silica gel with 4% ethyl acetate-hexane to give 9.2 g of yellow oil at a 92% yield.

Preparation of Compound 4: 4-[(2-Hydroxyethyl)ethylamino]-ethynylbenzene.

To a solution of 5.0 g, that is 15 mmole of 4-[(2-trimethylsiloxyethyl)ethylamino] trimethylsilylethynylbenzene, prepared in the previous step, dissolved in 60 mL of methanol-THF (1:1) mixture, 33 ml, that is 33 mmole, of 1M tetrabutylammonium fluoride in THF, from Aldrich Chemical Co. was added dropwise. The solution was stirred at room temperature for 1 hour. Ethyl ether was added and the mixture was extracted with water. The organic layer was separated, dried over anhydrous sodium sulfate and the solvent was removed under reduced pressure. The crude product was flash column chromatographed on silica gel with 35% ethyl acetate-hexane to produce 2.5 g of a viscous yellow oil at an 88% yield.

Preparation of Compound 5: 4-[(2-hydroxyethyl)ethylamino]-4'-(trifluoromethylsulfonyl)tolane.

A mixture containing 5.7 g, that is, 20 mmoles of 1-bromo-4-trifluoromethylsulfonyl benzene, produced according to the method disclosed in Nodiff, E. A. et. al. *J. Org. Chem.*, Vol. 25, p. 60 (1960), 0.63 g, that is 0.9 mmole bis(triphenylphosphine)palladium(II) chloride, 45 mg, that is 0.45 mmole cuprous chloride, and 18 g, that is, 180 mmole triethylamine in 80 m benzene was stirred and degassed under nitrogen for 15 minutes. The above mixture was maintained at 80° C. as a solution of 3.4 g that is 18 mmole 4-[(2-hydroxyethyl)ethylamino]ethynylbenzene, prepared in the previous step, in 40 ml of degassed benzene was added over a 20 minute period. The reaction was stirred for another 45 minutes and then filtered, extracted, followed by flash column chromatography on silica gel with 25% acetone-hexane. Recrystallization from ether-hexane mixture gave 5.9 g yellow needles, for a yield of 82%. The 4-[(2-hydroxyethyl)ethylamino]-4'-(trifluoromethylsulfonyl) tolane has a melting point of 183°–184° C., and NMR analysis revealed: NMR δ(CDCl$_3$) 7.96 (d, J=8.4 Hz, 2H), 7.70 (d, J=8.5 Hz, 2H), 7.42 (d, J=8.9 Hz, 2H), 6.72 (d, J=8.9 Hz, 2H), 3.84 (t, J=5.9 Hz, 2H), 3.56–3.44 (m, 4H), 1.20 (t, J=7.0 Hz, 3H).

Preparation of 4-[2-hydroxyethyl)ethylamino]-4'-(trifluoromethylsulfonyl) tolane - methacrylate monomer.

The monomer preparation was prepared as described in Example 1, using the photoabsorber 4-[(2-hydroxyethyl) ethylamino]-4'-(trifluoromethylsulfonyl)tolane. Purification by flash chromatography on silica gel with 18% acetone-hexane and recrystallization from ether-hexane gave pale yellow needles in 72% yield. The monomer has a melting point of 107°–108° C., and NMR analysis revealed δ(CDCl$_3$) 7.96 (d, J=8.5 Hz, 2H), 7.71 (d, J=8.5 Hz, 2H), 7.43 (d, J=8.9 Hz, 2H), 6.72 (d, J=8.9 Hz, 2H), 6.11 (s, 1H), 5.60 (t, J=1.5 Hz, 1H), 4.33 (t, J=6.3 Hz, 2H), 3.66 (t, J=6.3 Hz, 2H), 3.48 (q, J=7.0 Hz, 2H), 1.95 (s, 3H), 1.21 (t, J=7.0 Hz, 3H).

Polymerization of 4-[(2-hydroxyethyl)ethylamino]-4'-(trifluoromethylsulfonyl) tolane-methacrylate.

The ablatively photodecomposable polymer was prepared as described in Example 1. The resulting yellow polymer comprised of 93% methylmethacrylate and 7% 4-[(2-hydroxyethyl)ethylamino]-4'-(trifluoromethylsulfonyl) tolane-methacrylate, as established by NMR analysis has a molecular weight of 54,000, a dispersity of 1.7 and a Tg of 124° C.

EXAMPLE 6

The ablatively photodecomposable polymer having the following structure:

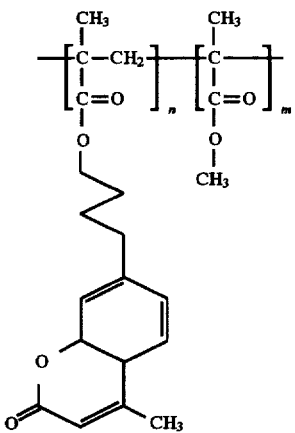

was prepared. The resulting copolymer comprised 70% methyl methacrylate and 30% 7-methacryloxy-4-2H-1-benzopyrene-2-1 absorber by weight.

Comparative Example A

For comparison, a sample was prepared in which polymethyl methacrylate was simply mixed with DR-1 photoabsorber.

Comparative Example B

For comparison, a sample was prepared of conventional polyimide ablatable composition which produces acceptable resolution.
Evaluation The polymer compositions of Examples 1–2E, 5–6, and the Comparative Examples A and B, were spin coated onto the metallized ceramic wafers. The substrate was then baked in a convection oven at 120° C. overnight to remove the solvent. The resulting film was smooth and hard and had a thickness of 2–3 microns. The polymer coating was excimer laser ablated at a wavelength of 308 nm, at 300 pulses/second, employing a fluence of 0.20 J/cm$^2$, and typically using 50 to 100 pulses, using a Lambda 2000 excimer laser from Lambda Physik Laser to form a circuit pattern in the ablatively photodecomposable polymer. The metal was etched by placing the patterned substrate into potassium permanganate, to remove the top layer of chromium, then placing the patterned substrate into a ferric chloride bath to remove the exposed copper and finally by placing the patterned substrate into a potassium permanganate bath, to remove the exposed chromium. Thus, metallization was entirely removed except the metallization protected by the ablatively photodecomposable polymer. The remaining ablatively photodecomposable polymer was selectively ablated to define structures such as copper pads. The structure was then etched only in potassium permanganate to remove the top layer of chromium and thereby expose copper. The structures were then examined visually.

All of the samples of the ablatively photodecomposable composition of Examples 1–2E and 5–6 demonstrated satisfactory ablation.

Figure 2:
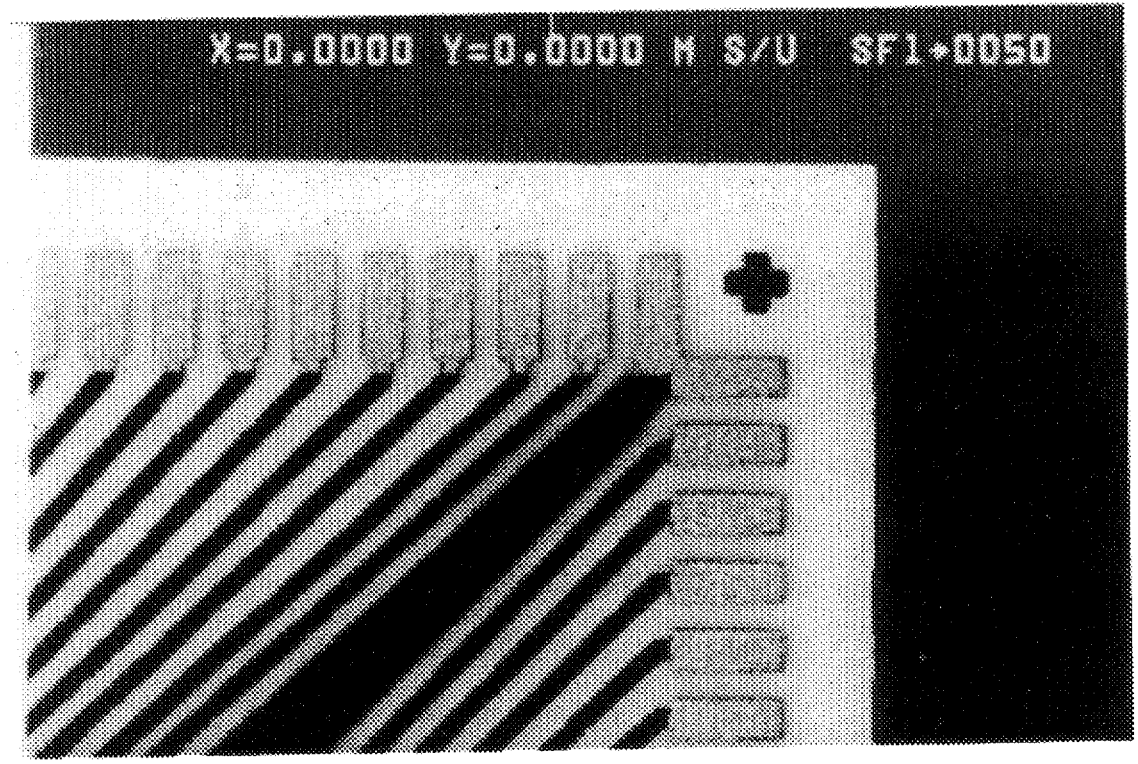
FIG. 2 is a photo of an outer lead bond formed by ablating DR1-PMMA.
Figure 3:
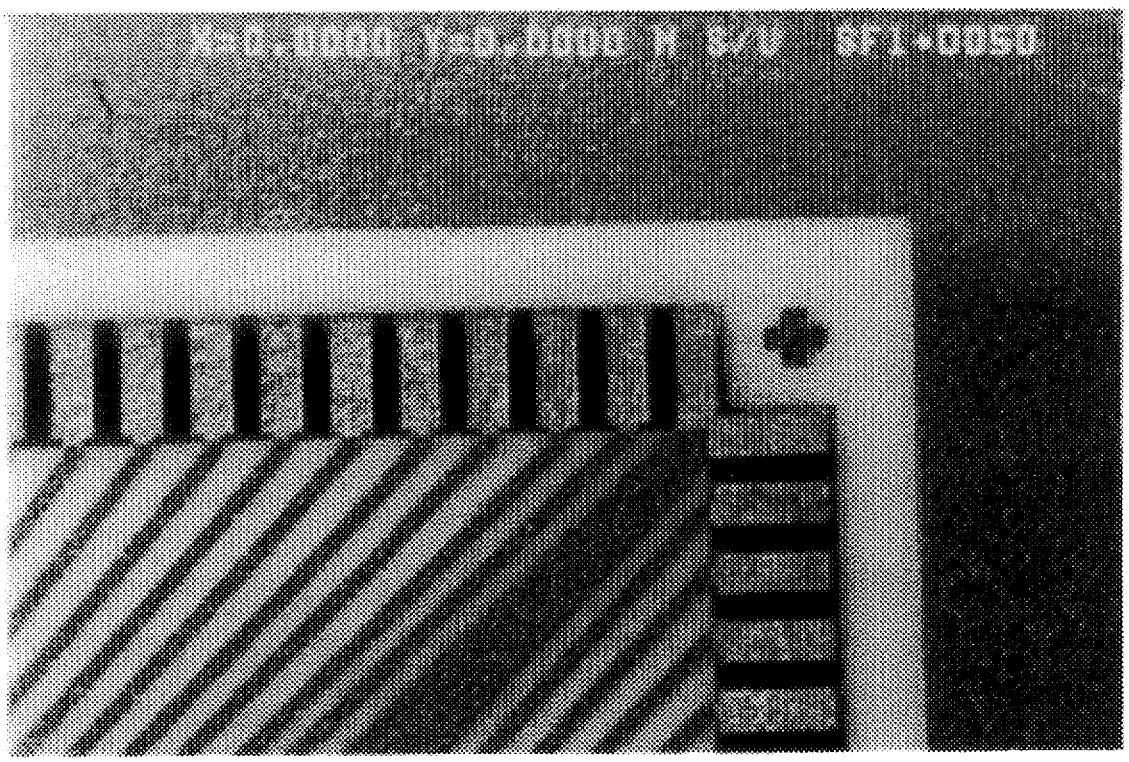
FIG. 3 is a photo of outer lead bonds formed by ablating polyimide.
Figure 4:
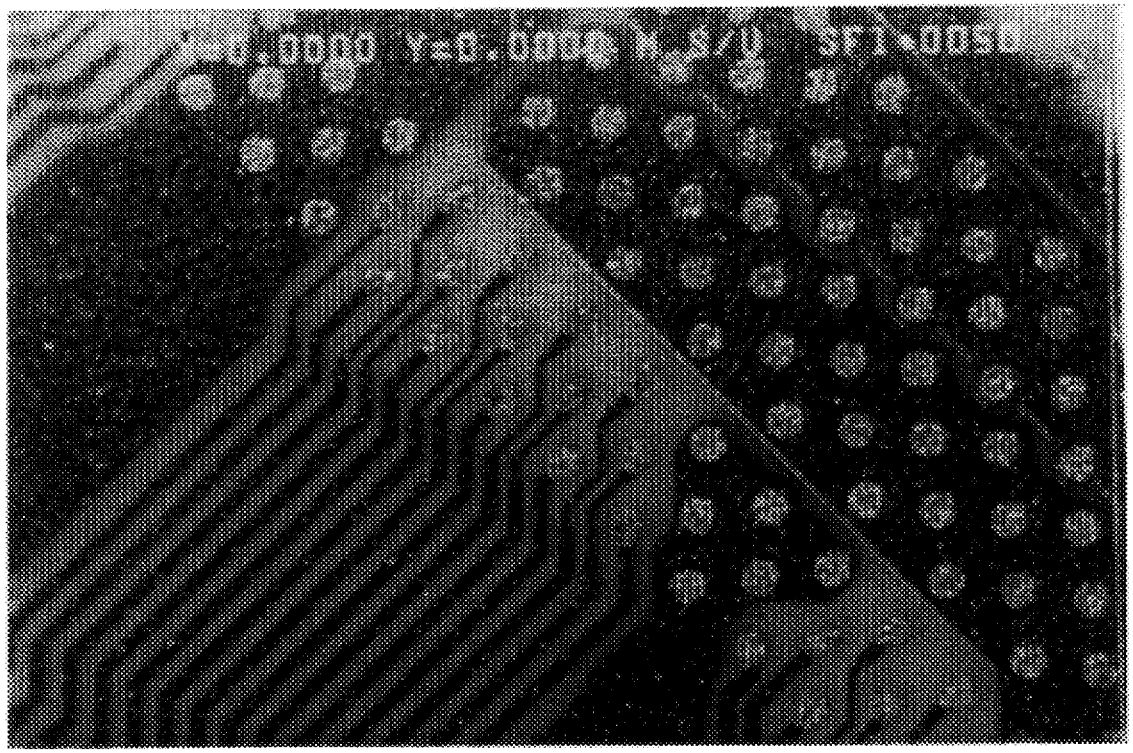
FIG. 4 is a portion of circuitization pattern showing chip site connection pads formed by ablating conventional polyimide.

FIGS. 3 and 4 show the structure coated with the ablatively photodecomposable polymer of Example 1 and FIGS. 1 and 2 show structures coated with the polyimide of Comparative Example B. The material of Comparative Example A (not shown) did not ablate well. However, carbon debris may be seen collecting between the outer lead bonds in FIG. 2, which is photograph of a substrate to which conventional polyimide had been applied. The debris is not present in FIG. 3. Thus, by employing the DR1-PMMA polymer the additional processing step of cleaning carbon debris is avoided.

Figure 5:
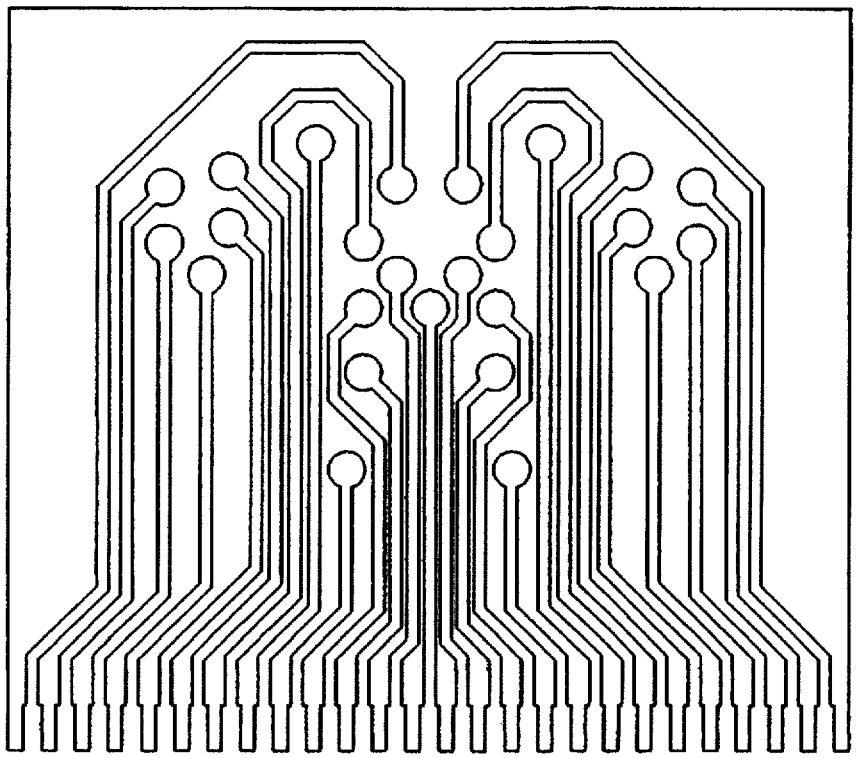
FIG. 5 is a drawing of a 7 mm×7 mm section of a circuitization pattern and metallized ceramic wafer in which the DR1-PMMA has been laser ablated.

The ablatively photodecomposable polymer of Example 1 was also coated onto metallized ceramic wafers having a thickness of 1 to 4 micrometers. Circuit patterns were then formed using either an excimer laser or deep UV lamp. The excimer laser operating at 308 nm and the pattern formed is shown in FIG. 5. The deep UV source was 300 watt UV lamp from Quintel Corp., at a wavelength of 253 nm, to form a line pattern in the ablatively photodecomposable composition, shown in FIG. 6.

Figure 6:
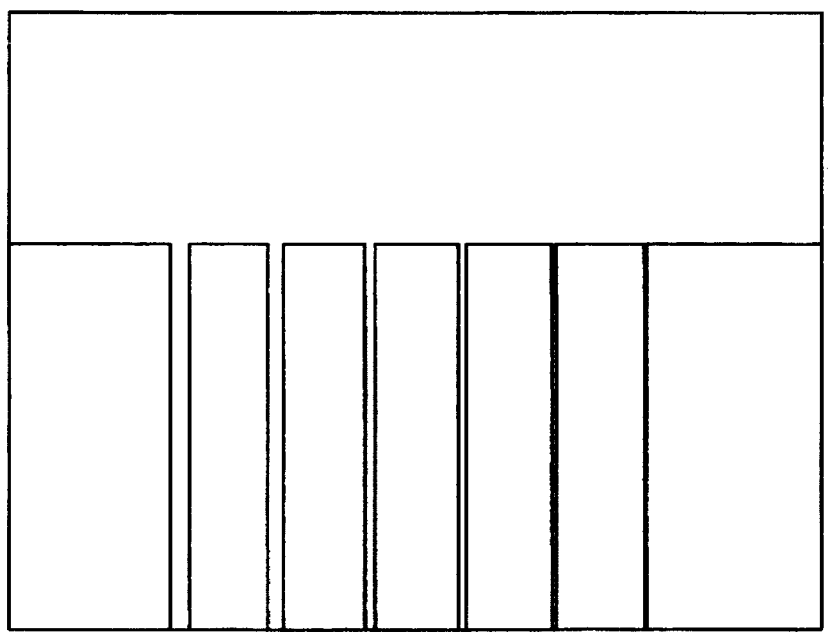
FIG. 6 is a drawing of a test line pattern produced on metallized ceramic substrates by photoablating PMMA-DR1 with deep ultraviolet light at 253 nm. The lines shown from left to right are 20, 16, 10, 8, 4, 2 μm wide.

The ablatively photodecomposable polymers of Examples 1, 2, 5 and 6 were defect-free and produced defect-free circuits. The line widths shown in FIG. 6 are comparable to line widths obtained using conventional lithographic processing.

The quality of the patterns formed by the ablatively photodecomposable polymer of Example 3 were significantly better than those formed by the DR-1-PMMA mixture of the Comparative Example.

The invention is not limited to the embodiments which have just been described. The invention is intended by the following claims to include all technically equivalent means which come within the full scope and true spirit of the invention.

What is claimed is:

1. A method for making 4-[(2-hydroxyethyl)ethylamino]-4'-(trifluoromethylsulfonyl)tolane comprising the following steps:

a. first providing (2-hydroxyethyl)ethylaniline;

b. iodinating the (2-hydroxyethyl)ethylaniline to produce 4-[(2-hydroxyethyl)ethylamino]iodobenzene;

c. adding a trimethylsilyl group to the 4-[(2-hydroxyethyl)ethylamino]iodobenzene to produce 4-[(2-trimethylsiloxyethyl)ethylamino]iodobenzene;

d. substituting a trimethylsilylethynyl group for the iodo group on 4-[(2-trimethylsiloxyethyl)-ethylamino]iodobenzene to produce 4-[(2-trimethylsiloxy-ethyl)ethylamino]trimethylsilylethynylbenzene;

e. removing the trimethylsilyl groups on the 4-[(2-trimethylsiloxyethyl)ethylamino]trimethylsilylethynylbenzene to produce 4-[(2-hydroxyethyl)ethylamino]ethynylbenzene;

f. adding 4-trifluoromethylsulfonyl benzene to 4-[(2-hydroxyethyl)ethylamino]ethynylbenzene to produce 4-[(2-hydroxyethyl)ethylamino]-4'-(trifluoromethylsulfonyl)tolane.

* * * * *